(12) United States Patent
Fukuoka et al.

(10) Patent No.: US 8,049,028 B2
(45) Date of Patent: *Nov. 1, 2011

(54) INDUSTRIAL PROCESS FOR SEPARATING OUT DIALKYL CARBONATE

(75) Inventors: Shinsuke Fukuoka, Tokyo (JP); Hironori Miyaji, Tokyo (JP); Hiroshi Hachiya, Tokyo (JP); Kazuhiko Matsuzaki, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 365 days.

This patent is subject to a terminal disclaimer.

(21) Appl. No.: 11/991,073

(22) PCT Filed: Dec. 15, 2006

(86) PCT No.: PCT/JP2006/325089
§ 371 (c)(1),
(2), (4) Date: Sep. 25, 2008

(87) PCT Pub. No.: WO2007/074664
PCT Pub. Date: Jul. 5, 2007

(65) Prior Publication Data
US 2009/0054676 A1 Feb. 26, 2009

(30) Foreign Application Priority Data

Dec. 26, 2005 (JP) .................................. 2005-371643

(51) Int. Cl.
*C07C 69/96* (2006.01)
(52) U.S. Cl. ...................................................... 558/277
(58) Field of Classification Search .................... 558/277
See application file for complete search history.

(56) References Cited

U.S. PATENT DOCUMENTS

| | | | |
|---|---|---|---|
| 3,642,858 A | 2/1972 | Frevel et al. | |
| 3,803,201 A | 4/1974 | Gilpin et al. | |
| 4,062,884 A | 12/1977 | Romano et al. | |
| 4,181,676 A | 1/1980 | Buysch et al. | |
| 4,307,032 A | 12/1981 | Krimm et al. | |
| 4,661,609 A | 4/1987 | Knifton | |
| 4,691,041 A | 9/1987 | Duranleau et al. | |
| 4,734,518 A | 3/1988 | Knifton | |
| 5,231,212 A | 7/1993 | Buysch et al. | |
| 5,359,118 A | 10/1994 | Wagner et al. | |
| 5,847,189 A | 12/1998 | Tojo et al. | |
| 6,346,638 B1 * | 2/2002 | Tojo et al. ..................... | 558/277 |
| 6,479,689 B1 | 11/2002 | Tojo et al. | |

FOREIGN PATENT DOCUMENTS

| | | |
|---|---|---|
| EP | 0530615 A2 | 8/1992 |
| EP | 0569812 A1 | 5/1993 |
| EP | 0889025 A1 | 1/1999 |
| EP | 1086940 A1 | 3/2001 |
| EP | 1174406 A1 | 1/2002 |
| EP | 1426086 A1 | 6/2004 |
| EP | 1 792 890 A1 | 6/2007 |
| EP | 1 795 523 A1 | 6/2007 |
| EP | 1953131 A1 | 8/2008 |
| EP | 1961721 A1 | 8/2008 |
| EP | 1961722 A1 | 8/2008 |
| EP | 1961723 A1 | 8/2008 |
| EP | 1961731 A1 | 8/2008 |
| EP | 1961732 A1 | 8/2008 |
| EP | 1964829 A1 | 9/2008 |
| EP | 1964831 A1 | 9/2008 |
| EP | 1967242 A1 | 9/2008 |
| EP | 1980548 A1 | 10/2008 |
| GB | 2109265 A | 6/1983 |
| JP | 51-122025 A | 10/1976 |
| JP | 54-48715 A | 4/1979 |
| JP | 54-48716 A | 4/1979 |
| JP | 54-63023 A | 5/1979 |
| JP | 54-148726 A | 11/1979 |
| JP | 63-41432 A | 2/1988 |
| JP | 63-238043 A | 10/1988 |
| JP | 64-31737 A | 2/1989 |
| JP | 04-198141 A | 7/1992 |
| JP | 04-230243 A | 8/1992 |
| JP | 5-213830 A | 8/1993 |
| JP | 6-9507 A | 1/1994 |
| JP | 06-196464 A | 7/1994 |
| JP | 6-228026 A | 8/1994 |
| JP | 07-25830 A | 1/1995 |
| JP | 09-176061 A | 7/1997 |
| JP | 09-183744 A | 7/1997 |
| JP | 09-194435 A | 7/1997 |
| JP | 2000-281630 A | 10/2000 |

(Continued)

OTHER PUBLICATIONS

European Application No. 06834816.8; European Search Report; Nov. 25, 2010; 3 pages.
Chinese Application No. 2006-80049253; Chinese Office Action, Apr. 14, 2011, pp. 1-3.
Computer generated English Translation of JP 06-228026 A. pp. 1-8, 1994.
Musch et al. "Robust PID control for an industrial distillation column" IEEE Control Systems, 1995, pp. 46-55.
U.S. Office Action for U.S. Appl. No. 11/991,251, dated Jun. 22, 2011.
Supplementary Eurpopean Search Report dated Aug. 5, 2011, for Application No. 06832900.2.

*Primary Examiner* — Rei-tsang Shiao
(74) *Attorney, Agent, or Firm* — Birch, Stewart, Kolasch & Birch, LLP

(57) ABSTRACT

It is an object of the present invention to provide a specific apparatus and process for using a single distillation column on a low boiling point reaction mixture containing a large amount of a dialkyl carbonate and an aliphatic monohydric alcohol produced through a reactive distillation process of taking a cyclic carbonate and the aliphatic monohydric alcohol as starting materials, continuously feeding the starting materials into a continuous multi-stage distillation column in which a homogeneous catalyst is present, and carrying out reaction and distillation simultaneously in the column, so as to separate the low boiling point reaction mixture by distillation into a column top component $B_T$ having the aliphatic monohydric alcohol as a main component thereof and a column bottom component $B_B$ having the dialkyl carbonate as a main component thereof stably for a prolonged period of time industrially.

18 Claims, 1 Drawing Sheet

FOREIGN PATENT DOCUMENTS

| | | | |
|---|---|---|---|
| JP | 2002-308804 A | 10/2002 |
| JP | 2002-371037 A | 12/2002 |
| JP | 2003-342209 A | 3/2003 |
| JP | 2003-119168 A | 4/2003 |
| JP | 2003-300936 A | 10/2003 |
| JP | 2004-131394 A | 4/2004 |
| JP | 2006-182683 A | 7/2006 |
| JP | 2006-199643 A | 8/2006 |
| JP | 2006-206497 A | 8/2006 |
| WO | WO-97/23445 A1 | 7/1997 |
| WO | WO-99/64382 A1 | 12/1999 |
| WO | WO-00/51954 A1 | 9/2000 |
| WO | WO-03/006418 A1 | 1/2003 |
| WO | 03/033450 A1 | 4/2003 |
| WO | WO-2005/123638 A1 | 12/2005 |
| WO | WO-2006-001256 A1 | 1/2006 |

\* cited by examiner

INDUSTRIAL PROCESS FOR SEPARATING OUT DIALKYL CARBONATE

TECHNICAL FIELD

The present invention relates to a process for subjecting a low boiling point reaction mixture containing a large amount of a dialkyl carbonate and an aliphatic monohydric alcohol produced through a reactive distillation process from a cyclic carbonate and the aliphatic monohydric alcohol to separation by distillation into a column top component $B_T$ having the aliphatic monohydric alcohol as a main component thereof and a column bottom component $B_B$ having the dialkyl carbonate as a main component thereof stably for a prolonged period of time industrially.

BACKGROUND ART

A reactive distillation process for producing a dialkyl carbonate and a diol through reaction between a cyclic carbonate and an aliphatic monohydric alcohol was first disclosed by the present inventors (see Patent Document 1: Japanese Patent Application Laid-Open No. H4-198141. Patent Document 2: Patent Document 13: Japanese Patent Application Laid-Open No. 2003-119168 (International Publication No. WO03/006418). Patent Document 14: Japanese Patent Application Laid-Open No. 2003-300936 and Patent Document 15: Japanese Patent Application Laid-Open No. 2003-342209). In the case of using a reactive distillation system for this reaction, the reaction can be made to proceed with a high conversion. However, reactive distillation processes proposed hitherto have related to producing the dialkyl carbonate and the diol either in small amounts or for a short period of time, and have not related to carrying out the production on an industrial scale stably for a prolonged period of time. That is, these processes have not attained the object of producing a dialkyl carbonate continuously in a large amount (e.g. not less than 2 ton/hr) stably for a prolonged period of time (e.g. not less than 1000 hours, preferably not less than 3000 hours, more preferably not less than 5000 hours).

For example, the maximum values of the height (H: cm), diameter (D: cm), and number of stages (n) of the reactive distillation column, the produced amount P (kg/hr) of dimethyl carbonate, and the continuous production time T (hr) in examples disclosed for the production of dimethyl carbonate (DMC) and ethylene glycol (EG) from ethylene carbonate and methanol are as in Table 1.

TABLE 1

| PATENT DOCUMENT | H:cm | D:cm | NO. STAGES:n | P:kg/hr | T:hr |
| --- | --- | --- | --- | --- | --- |
| 1 | 100 | 2 | 30 | 0.106 | 400 |
| 4 | 160 | 5 | 40 | 0.427 | NOTE 5 |
| 5 | 160 | 5 | 40 | 0.473 | NOTE 5 |
| 7 | 200 | 4 | PACKING COLUMN (Dixon) | 0.932 | NOTE 5 |
| 8 | NOTE 1 | 5 | 60 | 0.275 | NOTE 5 |
| 9 | NOTE 1 | 5 | 60 | 0.258 | NOTE 5 |
| 10 | NOTE 1 | 5 | 60 | 0.258 | NOTE 5 |
| 11 | 250 | 3 | PACKING COLUMN (Raschig) | 0.392 | NOTE 5 |
| 12 | NOTE 2 | NOTE 2 | NOTE 2 | 0.532 | NOTE 5 |
| 13 | NOTE 3 | NOTE 3 | 42 | NOTE 4 | NOTE 5 |
| 14 | NOTE 3 | NOTE 3 | 30 | 3750 | NOTE 5 |
| 15 | 200 | 15 | PACKING COLUMN (BX) | 0.313 | NOTE 5 |

NOTE 1: OLDERSHAW DISTILLATION COLUMN.
NOTE 2: NO DESCRIPTION WHATSOEVER DEFINING DISTILLATION COLUMN.
NOTE 3: ONLY DESCRIPTION DEFINING DISTILLATION COLUMN IS NUMBER OF STAGES.
NOTE 4: NO DESCRIPTION WHATSOEVER OF PRODUCED AMOUNT.
NOTE 5: NO DESCRIPTION WHATSOEVER REGARDING STABLE PRODUCTION FOR PROLONGED PERIOD OF TIME.

Japanese Patent Application Laid-Open No. H4-230243. Patent Document 3: Japanese Patent Application Laid-Open No. H9-176061. Patent Document 4: Japanese Patent Application Laid-Open No. H9-183744 Patent Document 5: Japanese Patent Application Laid-Open No. H9-194435. Patent Document 6: International Publication No. WO97/23445 (corresponding to European Patent No. 0889025, U.S. Pat. No. 5,847,189). Patent Document 7: International Publication No. WO99/64382 (corresponding to European Patent No. 1086940, U.S. Pat. No. 6,346,638). Patent Document 8: International Publication No. WO00/51954 (corresponding to European Patent No. 1174406, U.S. Pat. No. 6,479,689). Patent Document 9: Japanese Patent Application Laid-Open No. 2002-308804 and Patent Document 10: Japanese Patent Application Laid-Open No. 2004-131394), patent applications in which such a reactive distillation system is used have subsequently also been filed by other companies (see Patent Document 11: Japanese Patent Application Laid-Open No. H5-213830 (corresponding to European Patent No. 0530615, U.S. Pat. No. 5,231,212). Patent Document 12: Japanese Patent Application Laid-Open No. H6-9507 (corresponding to European Patent No. 0569812, U.S. Pat. No. 5,359,118).

In Patent Document 14 (Japanese Patent Application Laid-Open No. 2003-300936), it is stated at paragraph 0060 "The present example uses the same process flow as for the preferred mode shown in FIG. 1 described above, and was carried out with the object of operating a commercial scale apparatus for producing dimethyl carbonate and ethylene glycol through transesterification by a catalytic conversion reaction between ethylene carbonate and methanol. Note that the following numerical values in the present example can be adequately used in the operation of an actual apparatus", and as that example it is stated that 3750 kg/hr of dimethyl carbonate was specifically produced. The scale described in that example corresponds to an annual production of 30,000 tons or more, and hence this implies that at the time of the filing of the patent application for Patent Document 14 (Japanese Patent Application Laid-Open No. 2003-300936) (Apr. 9, 2002), operation of the world's first large scale commercial plant using this process had been carried out. However, even at the time of filing the present application, there is not the above fact at all. Moreover, in the example of Patent Document 14 (Japanese Patent Application Laid-Open No. 2003-300936), exactly the same value as the theoretically calculated value is stated for the amount of dimethyl carbonate produced, but the yield for ethylene glycol is approximately 85.6%, and the selectivity is approximately 88.4%, and hence it cannot really be said that a high yield and high selectivity have been attained. In particular, the low selectivity indicates that this process has a fatal drawback as an industrial production process. (Note also that Patent Document 14 (Japanese Patent Application Laid-Open No. 2003-300936) was deemed to have been withdrawn on Jul. 26, 2005 due to examination not having been requested).

With the reactive distillation method, there are very many causes of fluctuation such as composition variation due to reaction and composition variation due to distillation in the distillation column, and temperature variation and pressure variation in the column, and hence continuing stable operation for a prolonged period of time is accompanied by many difficulties, and in particular these difficulties are further increased in the case of handling large amounts. To continue mass production of a dialkyl carbonate and a diol using the reactive distillation method stably for a prolonged period of time while maintaining high yields and high selectivities for the dialkyl carbonate and the diol, the reactive distillation apparatus must be cleverly devised. However, the only description of continuous stable production for a prolonged period of time with the reactive distillation method proposed hitherto has been the 200 to 400 hours in Patent Document 1 (Japanese Patent Application Laid-Open No. H4-198141) and Patent Document 2 (Japanese Patent Application Laid-Open No. H4-230243).

The present inventors have now established an industrial reactive distillation process that enables a dialkyl carbonate and a diol to be mass-produced continuously and stably for a prolonged period of time with high yield and high selectivity, but to achieve this it has also been necessary to establish an industrial process for separating out the desired dialkyl carbonate from a low boiling point reaction mixture continuously withdrawn in a large amount from an upper portion of the reactive distillation column. The present invention has been devised to attain this object.

As shown in Table 1, with the exception of Patent Document 14 (Japanese Patent Application Laid-Open No. 2003-300936), the produced amount of the dialkyl carbonate per hour using reactive distillation processes proposed hitherto has been a small amount of not more than 1 kg/hr. Moreover, with the process of Patent Document 14 (Japanese Patent Application Laid-Open No. 2003-300936), a column top component (a mixture of methanol and dimethyl carbonate) from a first step reactive distillation column is fed into a second step distillation column, and extractive distillation is carried out using ethylene carbonate. After a mixture of ethylene carbonate and dimethyl carbonate has been obtained as a column bottom component from the second step distillation column, this mixture is then further fed into a third step distillation column, and separation by distillation is carried out so as to obtain dimethyl carbonate as a column top component and ethylene carbonate as a column bottom component from the third step distillation column. That is, with the process of Patent Document 14 (Japanese Patent Application Laid-Open No. 2003-300936), two columns must be used to separate the dimethyl carbonate out from the mixture of methanol and dimethyl carbonate, and hence the equipment is expensive. Furthermore, with this process, four distillation columns must be operated together with one another, and hence it is expected that prolonged stable operation would be difficult.

DISCLOSURE OF INVENTION

Problems to be Solved by the Invention

It is an object of the present invention to provide a specific apparatus and process for using a single distillation column on a low boiling point reaction mixture containing a large amount of a dialkyl carbonate and an aliphatic monohydric alcohol that has been produced through a reactive distillation process of taking a cyclic carbonate and the aliphatic monohydric alcohol as starting materials, continuously feeding the starting materials into a continuous multi-stage distillation column in which a homogeneous catalyst is present, and carrying out reaction and distillation simultaneously in the column, so as to separate the low boiling point reaction mixture by distillation into a column top component $B_T$ having the aliphatic monohydric alcohol as a main component thereof and a column bottom component $B_B$ having the dialkyl carbonate as a main component thereof stably for a prolonged period of time industrially. Moreover, it is an object to provide such a specific apparatus and process that are inexpensive and enable the dialkyl carbonate to be separated out by distillation in an amount of, for example, not less than 2 ton/hr stably for a prolonged period of time (e.g. not less than 1000 hours, preferably not less than 3000 hours, more preferably not less than 5000 hours).

Means for Solving the Problems

That is, according to the first aspect of the present invention, there are provided:

1. in an industrial process for separating out a dialkyl carbonate, comprising the steps of:

continuously feeding starting materials into a continuous multi-stage distillation column A in which a homogeneous catalyst is present by taking a cyclic carbonate and an aliphatic monohydric alcohol as the starting materials;

carrying out reactive distillation in said column A;

continuously withdrawing a high boiling point reaction mixture $A_B$ containing a produced diol from a lower portion of said column A in a liquid form;

continuously withdrawing a low boiling point reaction mixture $A_T$ containing a produced dialkyl carbonate and the aliphatic monohydric alcohol from an upper portion of said column A in a gaseous form;

continuously feeding said low boiling point reaction mixture $A_T$ into a continuous multi-stage distillation column B; and carrying out separation by distillation into a column top component $B_T$ having the aliphatic monohydric alcohol as a main component thereof and a column bottom component $B_B$ having the dialkyl carbonate as a main component thereof, wherein the improvement which comprises:

said continuous multi-stage distillation column B comprises a distillation column comprising a stripping section having a length $L_1$ (cm), an inside diameter $D_1$ (cm) and an internal with a number of stages $n_1$ thereinside, and an enrichment section having a length $L_2$ (cm), an inside diameter $D_2$ (cm) and an internal with a number of stages $n_2$ thereinside, wherein $L_1$, $D_1$, $n_1$, $L_2$, $D_2$, and $n_2$ satisfy the following formulae (1) to (8);

$$500 \leq L_1 \leq 3000 \tag{1}$$

$$100 \leq D_1 \leq 1000 \tag{2}$$

$$2 \leq L_1/D_1 \leq 30 \tag{3}$$

$$10 \leq n_1 \leq 40 \quad (4)$$

$$700 \leq L_2 \leq 5000 \quad (5)$$

$$50 \leq D_2 \leq 800 \quad (6)$$

$$10 \leq L_2/D_2 \leq 50 \quad (7), \text{ and}$$

$$35 \leq n_2 \leq 100 \quad (8),$$

2. the process according to item 1, wherein an amount of the dialkyl carbonate to be separated out is not less than 2 ton/hr,
3. the process according to item 1 or 2, wherein $L_1$, $D_1$, $L_1/D_1$, $n_1$, $L_2$, $D_2$, $L_2/D_2$, and $n_2$ for said continuous multi-stage distillation column B satisfy $800 \leq L_1 \leq 2500$, $120 \leq D_1 \leq 800$, $5 \leq L_1/D_1 \leq 20$, $13 \leq n_1 \leq 25$, $1500 \leq L_2 \leq 3500$, $70 \leq D_2 \leq 600$, $15 \leq L_2/D_2 \leq 30$, $40 \leq n_2 \leq 70$, $L_1 \leq L_2$, and $D_2 \leq D_1$,
4. the process according to any one of items 1 to 3, wherein the internal in each of the stripping section and the enrichment section of said continuous multi-stage distillation column B is a tray and/or a packing,
5. the process according to item 4, wherein the internal in each of the stripping section and the enrichment section of said continuous multi-stage distillation column B is the tray,
6. the process according to item 5, wherein said tray is a sieve tray,
7. the process according to item 6, wherein said sieve tray has 150 to 1200 holes/m² in a sieve portion thereof, and a cross-sectional area per hole is in a range of from 0.5 to 5 cm²,
8. the process according to item 6 or 7, wherein said sieve tray has 200 to 1100 holes/m² in said sieve portion thereof, and the cross-sectional area per hole is in a range of from 0.7 to 4 cm²,
9. the process according to any one of items 6 to 8, wherein said sieve tray has 250 to 1000 holes/m² in said sieve portion thereof, and the cross-sectional area per hole is in a range of from 0.9 to 3 cm²,
10. the process according to any one of items 1 to 9, wherein said continuous multi-stage distillation column B has a column bottom temperature in a range of from 150 to 250° C.,
11. the process according to any one of items 1 to 10, wherein said continuous multi-stage distillation column B has a reflux ratio in a range of from 0.5 to 5,
12. the process according to any one of items 1 to 11, wherein a concentration of the dialkyl carbonate in said column bottom component $B_B$ is not less than 97% by weight based on 100% by weight of said column bottom component,
13. the process according to any one of items 1 to 12, wherein a concentration of the dialkyl carbonate in said column bottom component $B_B$ is not less than 99% by weight based on 100% by weight of said column bottom component,
14. the process according to any one of items 1 to 13, wherein a concentration of the dialkyl carbonate in said column bottom component $B_B$ is not less than 99.9% by weight based on 100% by weight of said column bottom component,
15. the process according to any one of items 1 to 14, wherein said column top component $B_T$ is recycled as a starting material for producing the dialkyl carbonate and the diol,
16. the process according to any one of items 1 to 15, wherein the cyclic carbonate comprises ethylene carbonate and/or propylene carbonate, the aliphatic monohydric alcohol comprises methanol and/or ethanol, and the dialkyl carbonate to be separated out comprises dimethyl carbonate and/or diethyl carbonate.

Further, according to the second aspect of the present invention, there are provided:
17. a dialkyl carbonate separated out by the process according to any one of items 1 to 16, which comprises a halogen content of not more than 0.1 ppm,
18. a dialkyl carbonate separated out by the process according to any one of items 1 to 16, which comprises a halogen content of not more than 1 ppb,
19. the dialkyl carbonate according to item 17 or 18, which comprises an aliphatic monohydric alcohol content of not more than 0.1% by weight.

Furthermore, according to the third aspect of the present invention, there are provided:
20. a continuous multi-stage distillation column being a continuous multi-stage distillation column B for subjecting a low boiling point reaction mixture $A_T$ containing a produced dialkyl carbonate and an aliphatic monohydric alcohol to separation by distillation into a column top component $B_T$ having the aliphatic monohydric alcohol as a main component thereof and a column bottom component $B_B$ having the dialkyl carbonate as a main component thereof, the low boiling point reaction mixture $A_T$ having been obtained by taking a cyclic carbonate and the aliphatic monohydric alcohol as starting materials, continuously feeding the starting materials into a continuous multi-stage distillation column A in which a homogeneous catalyst is present, carrying out reactive distillation in the column A, continuously withdrawing a high boiling point reaction mixture $A_B$ containing a produced diol from a lower portion of the column in a liquid form, and continuously withdrawing the low boiling point reaction mixture $A_T$ from an upper portion of the column in a gaseous form, wherein
said continuous multi-stage distillation column B comprises:
a stripping section having a length $L_1$ (cm), an inside diameter $D_1$ (cm) and an internal with a number of stages $n_1$ thereinside; and
an enrichment section having a length $L_2$ (cm), an inside diameter $D_2$ (cm) and an internal with a number of stages $n_2$ thereinside;
wherein $L_1$, $D_1$, $n_1$, $L_2$, $D_2$, and $n_2$ satisfy the following formulae (1) to (8);

$$500 \leq L_1 \leq 3000 \quad (1)$$

$$100 \leq D_1 \leq 1000 \quad (2)$$

$$2 \leq L_1/D_1 \leq 30 \quad (3)$$

$$10 \leq n_1 \leq 40 \quad (4)$$

$$700 \leq L_2 \leq 5000 \quad (5)$$

$$50 \leq D_2 \leq 800 \quad (6)$$

$$10 \leq L_2/D_2 \leq 50 \quad (7), \text{ and}$$

$$35 \leq n_2 \leq 100 \quad (8),$$

21. the continuous multi-stage distillation column according to item 20, wherein $L_1$, $D_1$, $L_1/D_1$, $n_1$, $L_2$, $D_2$, $L_2/D_2$, and $n_2$ satisfy $800 \leq L_1 \leq 2500$, $120 \leq D_1 \leq 800$, $5 \leq L_1/D_1 \leq 20$, $13 \leq n_1 \leq 25$, $1500 \leq L_2 \leq 3500$, $70 \leq D_2 \leq 600$, $15 \leq L_2/D_2 \leq 30$, $40 \leq n_2 \leq 70$, $L_1 \leq L_2$, and $D_2 \leq D_1$,
22. the continuous multi-stage distillation column according to item 20 or 21, wherein the internal in each of the stripping section and the enrichment section is a tray and/or a packing, 23. the continuous multi-stage distillation column according to item 22, wherein the internal in each of the stripping section and the enrichment section is the tray,
24. the continuous multi-stage distillation column according to item 23, wherein said tray is a sieve tray,
25. the continuous multi-stage distillation column according to item 24, wherein said sieve tray has 150 to 1200 holes/m² in a sieve portion thereof, and a cross-sectional area per hole is in a range of from 0.5 to 5 cm²,
26. the continuous multi-stage distillation column according to item 24 or 25, wherein said sieve trays has 200 to 1100 holes/m² in said sieve portion thereof, and the cross-sectional area per hole is in a range of from 0.7 to 4 cm²,
27. the continuous multi-stage distillation column according to any one of items 24 to 26, wherein said sieve trays has 250 to 1000 holes/m² in said sieve portion thereof, and the cross-sectional area per hole is in a range of from 0.9 to 3 cm².

Advantageous Effects of Invention

By implementing the present invention, using a single distillation column B on a low boiling point reaction mixture $A_T$ containing a large amount of a dialkyl carbonate and an aliphatic monohydric alcohol that has been produced through a reactive distillation process of taking a cyclic carbonate and the aliphatic monohydric alcohol as starting materials, continuously feeding the starting materials into a continuous multi-stage distillation column A in which a homogeneous catalyst is present, and carrying out reaction and distillation simultaneously in the column, separation by distillation can be carried out into a column top component $B_T$ having the aliphatic monohydric alcohol as a main component thereof and a column bottom component $B_B$ having the dialkyl carbonate as a main component thereof stably for a prolonged period of time industrially. There have been discovered a specific apparatus and process that are inexpensive and enable the dialkyl carbonate to be separated out by distillation in an amount of, for example, not less than 2 ton/hr stably for a prolonged period of time (e.g. not less than 1000 hours, preferably not less than 3000 hours, more preferably not less than 5000 hours).

DESCRIPTION OF REFERENCE NUMERALS

Figure 1:
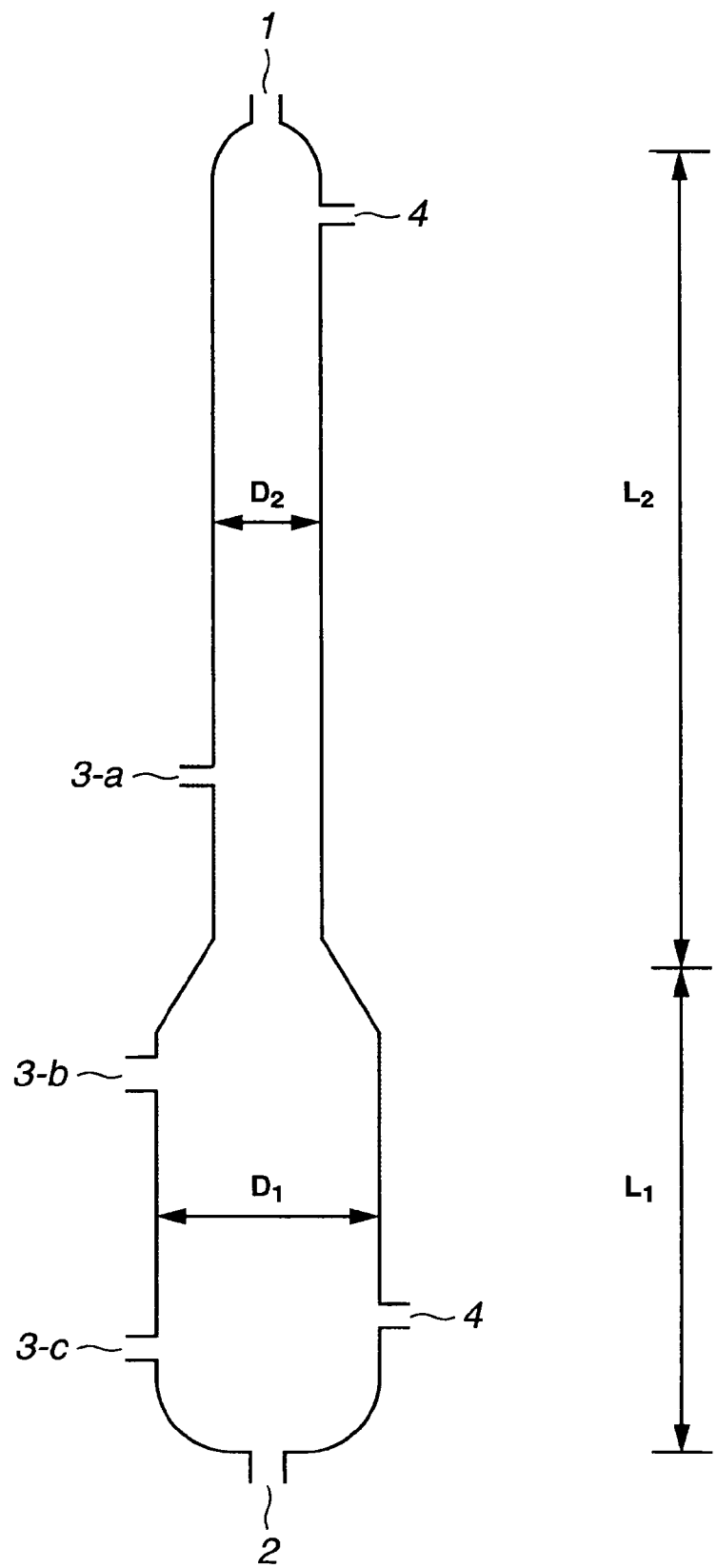
FIG. 1 is an example of schematic view of a continuous multi-stage distillation column B for carrying out the present invention, trays (not shown in FIG. 1) being installed as internals in each of a stripping section and an enrichment section in a trunk portion of the continuous multi-stage distillation column B.

1: gas outlet; 2: liquid outlet; 3-a to 3-c and 4: inlet; $L_1$: length (cm) of stripping section of the continuous multi-stage distillation column B; $L_2$: length (cm) of enrichment section of the continuous multi-stage distillation column B; D1: inside diameter (cm) of stripping section of the continuous multi-stage distillation column B; D2: inside diameter (cm) of enrichment of the continuous multi-stage distillation column B.

BEST MODE FOR CARRYING OUT THE INVENTION

Following is a detailed description of the present invention.
The reaction of the present invention is a reversible equilibrium transesterification reaction represented by following formula in which a dialkyl carbonate and a diol are produced from a cyclic carbonate and an aliphatic monohydric alcohol;

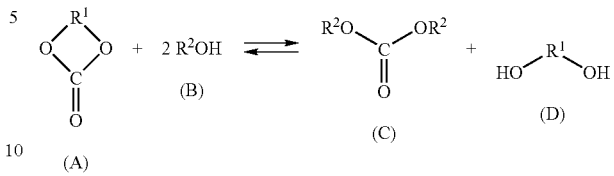

wherein $R^1$ represents a bivalent group —$(CH_2)_m$— (m is an integer from 2 to 6), one or more of the hydrogens thereof being optionally substituted with an alkyl group or aryl group having 1 to 10 carbon atoms. Moreover, $R^2$ represents a monovalent aliphatic group having 1 to 12 carbon atoms, one or more of the hydrogens thereof being optionally substituted with an alkyl group or aryl group having 1 to 10 carbon atoms.

The cyclic carbonate used as a starting material in the present invention is a compound represented by (A) in the above formula. For example, an alkylene carbonate such as ethylene carbonate or propylene carbonate, or 1,3-dioxacyclohexa-2-one, 1,3-dioxacyclohepta-2-one, or the like can be preferably used, ethylene carbonate or propylene carbonate being more preferably used due to ease of procurement and so on, and ethylene carbonate being particularly preferably used.

Moreover, the aliphatic monohydric alcohol used as the other starting material is a compound represented by (B) in the above formula. An aliphatic monohydric alcohol having a lower boiling point than that of the diol produced is used. Although possibly varying depending on the type of the cyclic carbonate used, examples are thus methanol, ethanol, propanol (isomers), allyl alcohol, butanol (isomers), 3-buten-1-ol, amyl alcohol (isomers), hexyl alcohol (isomers), heptyl alcohol (isomers), octyl alcohol (isomers), nonyl alcohol (isomers), decyl alcohol (isomers), undecyl alcohol (isomers), dodecyl alcohol (isomers), cyclopentanol, cyclohexanol, cycloheptanol, cyclooctanol, methylcyclopentanol (isomers), ethylcyclopentanol (isomers), methylcyclohexanol (isomers), ethylcyclohexanol (isomers), dimethylcyclohexanol (isomers), diethylcyclohexanol (isomers), phenylcyclohexanol (isomers), benzyl alcohol, phenethyl alcohol (isomers), phenylpropanol (isomers), and so on. Furthermore, these aliphatic monohydric alcohols may be substituted with substituents such as halogens, lower alkoxy groups, cyano groups, alkoxycarbonyl groups, aryloxycarbonyl groups, acyloxy groups, and nitro groups.

Of such aliphatic monohydric alcohols, ones preferably used are alcohols having 1 to 6 carbon atoms, more preferably alcohols having 1 to 4 carbon atoms, i.e. methanol, ethanol, propanol (isomers), and butanol (isomers). In the case of using ethylene carbonate or propylene carbonate as the cyclic carbonate, preferable aliphatic monohydric alcohols are methanol and ethanol, methanol being particularly preferable.

In the process according to the present invention, a homogeneous catalyst is made to be present in the reactive distillation column A. The method of making the homogeneous catalyst be present may be any method, but it is preferable to feed the catalyst into the reactive distillation column A continuously so as to make the catalyst be present in a liquid phase in the reactive distillation column A.

In the case that the homogeneous catalyst is continuously fed into the reactive distillation column A, the homogeneous catalyst may be fed in together with the cyclic carbonate and/or the aliphatic monohydric alcohol, or may be fed in at a different position to the starting materials. The reaction actually proceeds in the distillation column A in a region below the position at which the catalyst is fed in, and hence it is preferable to feed the catalyst into a region between the top of the column and the position(s) at which the starting materials are fed in. The catalyst must be present in at least 5 stages, preferably at least 7 stages, more preferably at least 10 stages.

As the catalyst used in the present invention, any of various catalysts known from hitherto can be used. Examples of the catalyst include;

alkali metals and alkaline earth metals such as lithium, sodium, potassium, rubidium, cesium, magnesium, calcium, strontium, and barium;

basic compounds of alkali metals and alkaline earth metals such as hydrides, hydroxides, alkoxides, aryloxides, and amides;

basic compounds of alkali metals and alkaline earth metals such as carbonates, bicarbonates, and organic acid salts;

tertiary amines such as triethylamine, tributylamine, trihexylamine, and benzyldiethylamine;

nitrogen-containing heteroaromatic compounds such as N-alkylpyrroles, N-alkylindoles, oxazoles, N-alkylimidazoles, N-alkylpyrazoles, oxadiazoles, pyridine, alkylpyridines, quinoline, alkylquinolines, isoquinoline, alkylisoquinolines, acridine, alkylacridines, phenanthroline, alkylphenanthrolines, pyrimidine, alkylpyrimidines, pyrazine, alkylpyrazines, triazines, and alkyltriazines;

cyclic amidines such as diazobicycloundecene (DBU) and diazobicyclononene (DBN);

thallium compounds such as thallium oxide, thallium halides, thallium hydroxide, thallium carbonate, thallium nitrate, thallium sulfate, and thallium organic acid salts;

tin compounds such as tributylmethoxytin, tributylethoxytin, dibutyldimethoxytin, diethyidiethoxytin, dibutyldiethoxytin, dibutylphenoxytin, diphenylmethoxytin, dibutyltin acetate, tributyltin chloride, and tin 2-ethylhexanoate;

zinc compounds such as dimethoxyzinc, diethoxyzinc, ethylenedioxyzinc, and dibutoxyzinc;

aluminum compounds such as aluminum trimethoxide, aluminum triisopropoxide, and aluminum tributoxide;

titanium compounds such as tetramethoxytitanium, tetraethoxytitanium, tetrabutoxytitanium, dichlorodimethoxytitanium, tetraisopropoxytitanium, titanium acetate, and titanium acetylacetonate;

phosphorus compounds such as trimethylphosphine, triethylphosphine, tributylphosphine, triphenylphosphine, tributylmethylphosphonium halides, trioctylbutylphosphonium halides, and triphenylmethylphosphonium halides;

zirconium compounds such as zirconium halides, zirconium acetylacetonate, zirconium alkoxides, and zirconium acetate;

lead and lead-containing compounds, for example lead oxides such as $PbO$, $PbO_2$, and $Pb_3O_4$;

lead sulfides such as $PbS$, $Pb_2S_3$, and $PbS_2$;

lead hydroxides such as $Pb(OH)_2$, $Pb_3O_2(OH)_2$, $Pb_2[PbO_2(OH)_2]$, and $Pb_2O(OH)_2$;

plumbites such as $Na_2PbO_2$, $K_2PbO_2$, $NaHPbO_2$, and $KHPbO_2$;

plumbates such as $Na_2PbO_3$, $Na_2H_2PbO_4$, $K_2PbO_3$, $K_2[Pb(OH)_6]$, $K_4PbO_4$, $Ca_2PbO_4$, and $CaPbO_3$;

lead carbonates and basic salts thereof such as $PbCO_3$ and $2PbCO_3.Pb(OH)_2$;

alkoxylead compounds and aryloxylead compounds such as $Pb(OCH_3)_2$, $(CH_3O)Pb(OPh)$, and $Pb(OPh)_2$;

lead salts of organic acids, and carbonates and basic salts thereof, such as $Pb(OCOCH_3)_2$, $Pb(OCOCH_3)_4$, and $Pb(OCOCH_3)_2.PbO._3H_2O$;

organolead compounds such as $Bu_4Pb$, $Ph_4Pb$, $Bu_3PbCl$, $Ph_3PbBr$, $Ph_3Pb$ (or $Ph_6Pb_2$), $Bu_3PbOH$, and $Ph_2PbO$ (wherein Bu represents a butyl group, and Ph represents a phenyl group);

lead alloys such as Pb—Na, Pb—Ca, Pb—Ba, Pb—Sn, and Pb—Sb; lead minerals such as galena and zinc blende; and hydrates of such lead compounds.

In the case that the compound used dissolves in a starting material of the reaction, the reaction mixture, a reaction by-product or the like, the compound can be used as the homogeneous catalyst as is. Alternatively, it is also preferable to use, as the homogeneous catalyst, a mixture obtained by dissolving a compound as above in a starting material of the reaction, the reaction mixture, a reaction by-product or the like in advance, or by reacting to bring about dissolution.

An amount of the catalyst used in the present invention varies depending on the type of the catalyst used, but is generally in a range of from 0.0001 to 50% by weight, preferably from 0.005 to 20% by weight, more preferably from 0.01 to 10% by weight, as a proportion of the total weight of the cyclic carbonate and the aliphatic monohydric alcohol fed in as the starting materials.

There are no particular limitations on the method of continuously feeding the cyclic carbonate and the aliphatic monohydric alcohol into a continuous multi-stage distillation column A constituting the reactive distillation column in the present invention; any feeding method may be used so long as the cyclic carbonate and the aliphatic monohydric alcohol can be made to contact the catalyst in a region of at least 5 stages, preferably at least 7 stages, more preferably at least 10 stages, of the distillation column A. That is, the cyclic carbonate and the aliphatic monohydric alcohol can be continuously fed in from a required number of inlets in stages of the continuous multi-stage distillation column A satisfying the conditions described earlier. Moreover, the cyclic carbonate and the aliphatic monohydric alcohol may be introduced into the same stage of the distillation column, or may be introduced into different stages to one another.

The starting materials are fed continuously into the distillation column A in a liquid form, in a gaseous form, or as a mixture of a liquid and a gas. Other than feeding the starting materials into the distillation column A in this way, it is also preferable to additionally feed in a gaseous starting material intermittently or continuously from a lower portion of the distillation column A. Moreover, another preferable method is one in which the cyclic carbonate is continuously fed in a liquid form or a gas/liquid mixed form into a stage of the distillation column above the stages in which the catalyst is present, and the aliphatic monohydric alcohol is continuously fed in a gaseous form and/or a liquid form into the lower portion of the distillation column. In this case, the cyclic carbonate may of course contain the aliphatic monohydric alcohol.

In the present invention, the starting materials fed in may contain the product dialkyl carbonate and/or diol. The content thereof is, for the dialkyl carbonate, generally in a range of from 0 to 40% by weight, preferably from 0 to 30% by weight, more preferably from 0 to 20% by weight, in terms of the percentage by mass of the dialkyl carbonate in the aliphatic monohydric alcohol/dialkyl carbonate mixture, and is, for the diol, generally in a range of from 0 to 10% by weight, preferably from 0 to 7% by weight, more preferably from 0 to 5% by weight, in terms of the percentage by mass of the diol in the cyclic carbonate/diol mixture.

When carrying out the present reaction industrially, besides fresh cyclic carbonate and/or aliphatic monohydric alcohol newly introduced into the reaction system, material having the cyclic carbonate and/or the aliphatic monohydric alcohol as a main component thereof recovered from this process and/or another process can also be preferably used for the starting materials. It is an excellent characteristic feature of the present invention that this is possible. An example of another process is a process in which a diaryl carbonate is produced from a dialkyl carbonate and an aromatic monohydroxy compound, the aliphatic monohydric alcohol being by-produced in this process and recovered. The recovered by-produced aliphatic monohydric alcohol generally often contains the dialkyl carbonate, the aromatic monohydroxy compound, an alkyl aryl ether and so on, and may also contain small amounts of an alkyl aryl carbonate, the diaryl carbonate and so on. The by-produced aliphatic monohydric alcohol may be used as is as a starting material in the present invention, or may be used as the starting material after amount of contained material having a higher boiling point than that of the aliphatic monohydric alcohol has been reduced through distillation or the like.

Moreover, a cyclic carbonate preferably used in the present invention is one produced through reaction between, for example, an alkylene oxide such as ethylene oxide, propylene oxide or styrene oxide and carbon dioxide; a cyclic carbonate containing small amounts of these raw material compounds or the like may be used as a starting material in the present invention.

In the present invention, a ratio between the amounts of the cyclic carbonate and the aliphatic monohydric alcohol fed into the reactive distillation column varies according to the type and amount of the transesterification catalyst and the reaction conditions, but a molar ratio of the aliphatic monohydric alcohol to the cyclic carbonate fed in is generally in a range of from 0.01 to 1000 times. To increase the cyclic carbonate conversion, it is preferable to feed in the aliphatic monohydric alcohol in an excess of at least 2 times the number of mols of the cyclic carbonate, but if the amount of the aliphatic monohydric alcohol used is too great, then it is necessary to make the apparatus larger. For such reasons, the molar ratio of the aliphatic monohydric alcohol to the cyclic carbonate is preferably in a range of from 2 to 20, more preferably from 3 to 15, yet more preferably from 5 to 12. Furthermore, if much unreacted cyclic carbonate remains, then the unreacted cyclic carbonate may react with the product diol to by-produce oligomers such as a dimer or a trimer, and hence in industrial implementation, it is preferable to reduce the amount of unreacted cyclic carbonate remaining as much as possible. In the process of the present invention, even if the above molar ratio is not more than 10, the cyclic carbonate conversion can be made to be not less than 98%, preferably not less than 99%, more preferably not less than 99.9%. This is another characteristic feature of the present invention.

In the present invention, preferably not less than 2 ton/hr of the dialkyl carbonate is continuously produced to be subjected to the separation by distillation in use of the continuous multi-stage distillation column B; the minimum amount of the cyclic carbonate continuously fed in to achieve this is generally 2.2 P ton/hr, preferably 2.1 P ton/hr, more preferably 2.0 P ton/hr, based on the amount P (ton/hr) of the dialkyl carbonate to be produced. In a yet more preferable case, this amount can be made to be less than 1.9 P ton/hr.

There are no particular limitations on the continuous multi-stage distillation column A for carrying out the reactive distillation process in the present invention, but the continuous multi-stage distillation column A must be a continuous multi-stage distillation column that enables not only distillation but also reaction to be carried out at the same time so as to be able to produce preferably not less than 2 ton/hr of the dialkyl carbonate and/or preferably not less than 1.3 ton/hr of the diol stably for a prolonged period of time.

In the present invention, the cyclic carbonate and the aliphatic monohydric alcohol are taken as starting materials, the starting materials are continuously fed into the continuous multi-stage distillation column A in which the homogeneous catalyst is present, reactive distillation is carried out in the column A, a high boiling point reaction mixture $A_B$ containing a produced diol is continuously withdrawn from a lower portion of the column A in a liquid form, and a low boiling point reaction mixture $A_T$ containing a produced dialkyl carbonate and the aliphatic monohydric alcohol is continuously withdrawn from an upper portion of the column A in a gaseous form, and a continuous multi-stage distillation column B is used to subject the low boiling point reaction mixture $A_T$ to separation by distillation into a column top component $B_T$ having the aliphatic monohydric alcohol as a main component thereof and a column bottom component $B_B$ having the dialkyl carbonate as a main component thereof.

The continuous multi-stage distillation column B used in the present invention must have a function of separating out the dialkyl carbonate with a prescribed separation efficiency stably for a prolonged period of time from a large amount of the reaction mixture, and various conditions must be simultaneously satisfied to achieve this.

Specifically, the continuous multi-stage distillation column B is a distillation column comprising a stripping section having a length $L_1$ (cm), an inside diameter $D_1$ (cm) and an internal with a number of stages $n_1$ thereinside, and an enrichment section having a length $L_2$ (cm), an inside diameter $D_2$ (cm) and an internal with a number of stages $n_2$ thereinside, wherein $L_1$, $D_1$, $n_1$, $L_2$, $D_2$, and $n_2$ satisfy the following formulae (1) to (8);

$$500 \leq L_1 \leq 3000 \tag{1}$$

$$100 \leq D_1 \leq 1000 \tag{2}$$

$$2 \leq L_1/D_1 \leq 30 \tag{3}$$

$$10 \leq n_1 \leq 40 \tag{4}$$

$$700 \leq L_2 \leq 5000 \tag{5}$$

$$50 \leq D_2 \leq 800 \tag{6}$$

$$10 \leq L_2/D_2 \leq 50 \tag{7, and}$$

$$35 \leq n_2 \leq 100 \tag{8}.$$

It has been discovered that by using such a continuous multi-stage distillation column B simultaneously satisfying the formulae (1) to (8), a dialkyl carbonate can be separated out and purified as a column bottom component $B_B$ at a purity of not less than 97% by weight on an industrial scale of preferably not less than 2 ton/hr stably for a prolonged period of time of, for example, not less than 1000 hours, preferably not less than 3000 hours, more preferably not less than 5000 hours from a large amount of a low boiling point reaction mixture $A_T$ that has been produced through reactive distillation between a cyclic carbonate and an aliphatic monohydric alcohol. Regarding the purity of the dialkyl carbonate separated out, generally a high purity of not less than 97% by weight, preferably not less than 99% by weight, can be easily attained. In the present invention, it is also easy to make the purity of the dialkyl carbonate obtained as the column bottom component be an ultra-high purity of preferably not less than 99.9% by weight, more preferably not less than 99.99% by weight. The reason why it has become possible to separate out and purify the dialkyl carbonate on an industrial scale with such excellent effects by implementing the process of the present invention is not clear, but this is supposed to be due to a composite effect brought about when the conditions of the formulae (1) to (8) are combined.

Preferable ranges for the respective factors are described below.

If $L_1$ (cm) is less than 500, then the separation efficiency for the stripping section decreases, and hence the desired separation efficiency cannot be attained. Moreover, to keep down the equipment cost while securing the desired separation efficiency, $L_1$ must be made to be not more than 3000. A more preferable range for $L_1$ (cm) is $800 \leq L_1 \leq 2500$, with $1000 \leq L_1 \leq 2000$ being yet more preferable.

If $D_1$ (cm) is less than 100, then it is not possible to attain the desired distillation amount. Moreover, to keep down the equipment cost while attaining the desired distillation amount, $D_1$ must be made to be not more than 1000. A more preferable range for $D_1$ (cm) is $120 \leq D_1 \leq 800$, with $150 \leq D_1 \leq 600$ being yet more preferable.

If $L_1/D_1$ is less than 2 or greater than 30, then prolonged stable operation becomes difficult. A more preferable range for $L_1/D_1$ is $5 \leq L_1/D_1 \leq 20$, with $7 \leq L_1/D_1 \leq 15$ being yet more preferable.

If $n_1$ is less than 10, then the separation efficiency for the stripping section decreases and hence the desired separation efficiency cannot be attained. Moreover, to keep down the equipment cost while securing the desired separation efficiency, $n_1$ must be made to be not more than 40. A more preferable range for $n_1$ is $13 \leq n_1 \leq 25$, with $15 \leq n_1 \leq 20$ being yet more preferable.

If $L_2$ (cm) is less than 700, then the separation efficiency for the enrichment section decreases, and hence the desired separation efficiency cannot be attained. Moreover, to keep down the equipment cost while securing the desired separation efficiency, $L_2$ must be made to be not more than 5000. Furthermore, if $L_2$ is greater than 5000, then the pressure difference between the top and bottom of the column becomes too great, and hence prolonged stable operation becomes difficult. Moreover, it becomes necessary to increase the temperature in the lower portion of the column, and hence side reactions become liable to occur. A more preferable range for $L_2$ (cm) is $1500 \leq L_2 \leq 3500$, with $2000 \leq L_2 \leq 3000$ being yet more preferable.

If $D_2$ (cm) is less than 50, then it is not possible to attain the desired distillation amount. Moreover, to keep down the equipment cost while attaining the desired distillation amount, $D_2$ must be made to be not more than 800. A more preferable range for $D_2$ (cm) is $70 \leq D_2 \leq 600$, with $80 \leq D_2 \leq 400$ being yet more preferable.

If $L_2/D_2$ is less than 10 or greater than 50, then prolonged stable operation becomes difficult. A more preferable range for $L_2/D_2$ is $15 \leq L_2/D_2 \leq 30$, with $20 \leq L_2/D_2 \leq 28$ being yet more preferable.

If $n_2$ is less than 35, then the separation efficiency for the enrichment section decreases and hence the desired separation efficiency cannot be attained. Moreover, to keep down the equipment cost while securing the desired separation efficiency, $n_2$ must be made to be not more than 100. Furthermore, if $n_2$ is greater than 100, then the pressure difference between the top and bottom of the column becomes too great, and hence prolonged stable operation becomes difficult. Moreover, it becomes necessary to increase the temperature in the lower portion of the column, and hence side reactions become liable to occur. A more preferable range for $n_2$ is $40 \leq n_2 \leq 70$, with $45 \leq n_2 \leq 65$ being yet more preferable.

Moreover, for the continuous multi-stage distillation column B in the present invention, preferably $L_1 \leq L_2$, more preferably $L_1 < L_2$. Furthermore, preferably $D_2 \leq D_1$, more preferably $D_2 < D_1$. In the present invention, the case that $L_1 \leq L_2$ and $D_2 \leq D_1$ is thus preferable, the case that $L_1 < L_2$ and $D_2 < D_1$ being more preferable.

In the present invention, the continuous multi-stage distillation column B is preferably a distillation column having trays and/or packings as the internal in each of the stripping section and the enrichment section. The term "internal" used in the present invention means the part in the distillation column where gas and liquid are actually brought into contact with one another. Examples of the trays include a bubble-cap tray, a sieve tray, a ripple tray, a ballast tray, a valve tray, a counterflow tray, an Unifrax tray, a Superfrac tray, a Maxfrac tray, a dual flow tray, a grid plate tray, a turbogrid plate tray, a Kittel tray, or the like. Examples of the packings include random packings such as a Raschig ring, a Lessing ring, a Pall ring, a Berl saddle, an Intalox saddle, a Dixon packing, a McMahon packing or Heli-Pak, or structured packings such as Mellapak, Gempak, Techno-pack, Flexipac, a Sulzer packing, a Goodroll packing or Glitschgrid. A multi-stage distillation column having both a tray portion and a portion packed with packings can also be used. Furthermore, the term "number of stages n of the internals" used in the present invention means the number of trays in the case of trays, and the theoretical number of stages in the case of packings. The number of stages n in the case of a continuous multi-stage distillation column having both a tray portion and a portion packed with packings is thus the sum of the number of trays and the theoretical number of stages.

In the present invention, it is particularly preferable for the internal in both the stripping section and the enrichment section of the continuous multi-stage distillation column B to be tray. Furthermore, it has been discovered that sieve trays each having a sieve portion and a downcomer portion are particularly good as the tray in terms of the relationship between performance and equipment cost. It has also been discovered that each sieve tray preferably has 150 to 1200 holes/m² in the sieve portion. A more preferable number of holes is from 200 to 1100 holes/m², yet more preferably from 250 to 1000 holes/m². Moreover, it has been discovered that the cross-sectional area per hole of each sieve tray is preferably in a range of from 0.5 to 5 cm². A more preferable cross-sectional area per hole is from 0.7 to 4 cm², yet more preferably from 0.9 to 3 cm². Furthermore, it has been discovered that it is particularly preferable if each sieve tray has 150 to 1200 holes/m² in the sieve portion, and the cross-sectional area per hole is in a range of from 0.5 to 5 cm². It has been shown that by adding the above conditions to the continuous multi-stage distillation column B, the object of the present invention can be attained more easily.

In the present invention, the dialkyl carbonate produced through the reactive distillation in the continuous multi-stage distillation column A is continuously withdrawn from the upper portion of the column in a gaseous form as the low boiling point reaction mixture $A_T$ together with aliphatic monohydric alcohol that has remained unreacted due to generally being used in excess. The low boiling point reaction mixture $A_T$ is continuously fed into the continuous multi-stage distillation column B, a low boiling point mixture $B_T$ having the aliphatic monohydric alcohol as a main component thereof is continuously withdrawn from an upper portion of the column in a gaseous form, and a high boiling point mixture $B_B$ having the dialkyl carbonate as a main component thereof is continuously withdrawn from a lower portion of the column in a liquid form. When feeding the low boiling point reaction mixture $A_T$ into the continuous multi-stage distillation column B, the low boiling point reaction mixture $A_T$ may be fed in in a gaseous form, or in a liquid form. It is preferable to heat or cool the low boiling point reaction mixture $A_T$ to a temperature close to the liquid temperature in the vicinity of the feeding inlet of the continuous multi-stage distillation column B before feeding the low boiling point reaction mixture $A_T$ into the distillation column B.

Moreover, the position from which the low boiling point reaction mixture $A_T$ is fed into the continuous multi-stage distillation column B is preferably around between the stripping section and the enrichment section. The continuous multi-stage distillation column B preferably has a reboiler for heating the distillate, and a refluxing apparatus.

In the present invention, the low boiling point reaction mixture $A_T$ is generally withdrawn from the continuous multi-stage distillation column A in an amount of not less than 2 ton/hr, before being fed into the continuous multi-stage distillation column B and thus subjected to the separation by distillation, whereupon the low boiling point mixture $B_T$ is continuously withdrawn from the upper portion of the distillation column B, and the high boiling point mixture $B_B$ is continuously withdrawn from the lower portion of the distillation column B.

In the present invention, the concentration of the aliphatic monohydric alcohol in the low boiling point mixture $B_T$ can be made to be not less than 80% by weight, preferably not less than 85% by weight, more preferably not less than 90% by weight. Moreover, the concentration of the dialkyl carbonate in the high boiling point mixture $B_B$ can easily be made to be not less than 97% by weight, preferably not less than 99% by weight, more preferably not less than 99.9% by weight, yet more preferably not less than 99.99% by weight. Furthermore, the amount of the alcohol separated out as the main component of the low boiling point mixture $B_T$ is generally not less than 500 kg/hr, preferably not less than 1 ton/hr, more preferably not less than 2 ton/hr. The remainder of the low boiling point mixture $B_T$ is mostly the dialkyl carbonate, and hence the low boiling point mixture $B_T$ can be reused as aliphatic monohydric alcohol for reacting with the cyclic carbonate either as is or else after having been mixed with alcohol recovered from another process. This is one preferable embodiment of the present invention. In the case that the amount of recovered alcohol is insufficient, fresh aliphatic monohydric alcohol may be added.

The high boiling point mixture $B_B$ separated off in the present invention has the dialkyl carbonate as the main component thereof, and has a content of unreacted aliphatic monohydric alcohol of not more than 3% by weight, preferably not more than 1% by weight, more preferably not more than 0.1% by weight, yet more preferably not more than 0.01% by weight. Moreover, in a preferable embodiment of the present invention, the reaction is carried out using starting materials and catalyst not containing a halogen, and hence the produced dialkyl carbonate can be made to not contain a halogen at all. In the present invention, a high-purity dialkyl carbonate of concentration not less than 97% by weight, preferably not less than 99% by weight, more preferably not less than 99.9% by weight, yet more preferably not less than 99.99% by weight, with a halogen content of not more than 0.1 ppm, preferably not more than 1 ppb, can thus be easily obtained.

The distillation conditions for the continuous multi-stage distillation column B used in the present invention vary depending on the form of the internals in the distillation column and the number of stages, the type, composition and amount of the low boiling point reaction mixture $A_T$ fed in, the purity of the dialkyl carbonate to be obtained through the separation, and so on. The column bottom temperature is generally a specified temperature in a range of from 150 to 250° C. A more preferable temperature range is from 170 to 230° C., yet more preferably from 180 to 220° C. The column bottom pressure varies depending on the composition in the column and the column bottom temperature used, but in the present invention the continuous multi-stage distillation column B is generally operated under an applied pressure.

Moreover, the reflux ratio for the continuous multi-stage distillation column B is preferably in a range of from 0.5 to 5, more preferably from 0.8 to 3, yet more preferably from 1 to 2.5.

The material constituting each of the continuous multi-stage distillation columns A and B used in the present invention is generally a metallic material such as carbon steel or stainless steel. In terms of the quality of the dialkyl carbonate and diol produced and subjected to the separation, stainless steel is preferable.

EXAMPLES

Following is a more detailed description of the present invention through examples. However, the present invention is not limited to the following examples.

Example 1

A continuous multi-stage distillation column B as shown in FIG. 1 having $L_1=1600$ cm, $D_1=260$ cm, $L_1/D_1=6.2$, $n_1=18$, $L_2=2700$ cm, $D_2=160$ cm, $L_2/D_2=16.9$, and $n_2=58$ was used. In this example, sieve trays were used as the internals in both the stripping section and the enrichment section (cross-sectional area per hole=approximately 1.3 $cm^2$, number of holes=approximately 300 to 440/$m^2$).

A starting material containing ethylene carbonate (EC) and methanol (MeOH) (molar ratio MeOH/EC=8.4) and a catalyst (KOH in ethylene glycol subjected to thermal dehydration treatment; K concentration 0.1% by weight based on EC) was continuously fed into a continuous multi-stage distillation column A, and reactive distillation was carried out, whereby 8.18 ton/hr of a column top component $A_T$ was continuously withdrawn. The column top component $A_T$, which contained 4.644 ton/hr of methanol and 3.536 ton/hr of dimethyl carbonate, was continuously fed into the continuous multi-stage distillation column B from an inlet 3-*b*. This inlet was provided between the trays in the 18$^{th}$ and 19$^{th}$ stages from the bottom of the continuous multi-stage distillation column B.

The continuous multi-stage distillation column B was operated continuously with a column bottom temperature of approximately 205° C., a column bottom pressure of approximately 1.46 MPa, and a reflux ratio of approximately 1.8.

It was possible to attain stable steady state operation after 24 hours. A column top component $B_T$ continuously withdrawn from the top 1 of the continuous multi-stage distillation column B at 5.08 ton/hr contained 4.644 ton/hr of methanol and 0.436 ton/hr of dimethyl carbonate. The methanol concentration in the column top component $B_T$ was 91.42% by weight. Moreover, a column bottom component $B_B$ continuously withdrawn from the bottom 2 of the continuous multi-stage distillation column B at 3.1 ton/hr contained not less than 99.99% by weight of dimethyl carbonate (methanol content not more than 0.01% by weight).

This means that of the dimethyl carbonate fed into the continuous multi-stage distillation column B, approximately 87.7% was obtained as high-purity dimethyl carbonate. Note that the column top component $B_T$ was fed as is into the reactive distillation column A, and thus used as some of the starting material for producing the dimethyl carbonate and the diol.

Prolonged continuous operation was carried out under these conditions. After 500 hours, 2000 hours, 4000 hours, 5000 hours, and 6000 hours, the produced amounts of dimethyl carbonate per hour were 3.1 ton, 3.1 ton, 3.1 ton, 3.1 ton, and 3.1 ton, and hence operation was very stable. The purity of the dimethyl carbonate obtained through the separation/purification was 99.99% in each case, and the halogen content was outside the detection limit, i.e. not more than 1 ppb.

Example 2

Reactive distillation and dimethyl carbonate separation/purification were carried out using the same continuous multi-stage distillation column B and the same process as in Example 1. The column top component $A_T$, which was continuously withdrawn from the top of the continuous multi-stage distillation column A (reactive distillation column) at 12.27 ton/hr, contained 6.967 ton/hr of methanol and 5.303 ton/hr of dimethyl carbonate. This column top component $A_T$ was continuously fed into the continuous multi-stage distillation column B from an inlet 3-b.

It was possible to attain stable steady state operation after 24 hours. The column top component $B_T$, which was continuously withdrawn from the top 1 of the continuous multi-stage distillation column B at 7.62 ton/hr, contained 6.967 ton/hr of methanol and 0.654 ton/hr of dimethyl carbonate. The methanol concentration in the column top component $B_T$ was 91.43% by weight. Moreover, the column bottom component $B_B$, which was continuously withdrawn from the bottom 2 of the continuous multi-stage distillation column B at 4.65 ton/hr, contained not less than 99.99% by weight of dimethyl carbonate (methanol content not more than 0.01% by weight).

This means that of the dimethyl carbonate fed into the continuous multi-stage distillation column B, approximately 87.7% was obtained as high-purity dimethyl carbonate. Note that the column top component $B_T$ was fed as is into the reactive distillation column A, and thus used as some of the starting material for producing the dimethyl carbonate and the diol.

Prolonged continuous operation was carried out under these conditions. After 500 hours, 2000 hours, 4000 hours, 5000 hours, and 6000 hours, the produced amounts of dimethyl carbonate per hour were 4.65 ton, 4.65 ton, 4.65 ton, 4.65 ton, and 4.65 ton, and hence operation was very stable. The purity of the dimethyl carbonate obtained through the separation/purification was 99.99% in each case, and the halogen content was outside the detection limit, i.e. not more than 1 ppb.

Example 3

A continuous multi-stage distillation column B as shown in FIG. 1 was used. In this example, sieve trays were used as the internals in both the stripping section and the enrichment section (cross-sectional area per hole=approximately 1.3 cm², number of holes=approximately 530 to 800/m²).

Reactive distillation and dimethyl carbonate separation/purification were carried out using the same process as in Example 1. The column top component $A^T$, which was continuously withdrawn from the top of the continuous multi-stage distillation column A (reactive distillation column) at 24.54 ton/hr, contained 13.934 ton/hr of methanol and 10.606 ton/hr of dimethyl carbonate. This column top component $A_T$ was continuously introduced into the continuous multi-stage distillation column B from an inlet 3-b.

It was possible to attain stable steady state operation after 24 hours. The column top component $B_T$, which was continuously withdrawn from the top 1 of the continuous multi-stage distillation column B at 15.24 ton/hr, contained 13.934 ton/hr of methanol and 1.306 ton/hr of dimethyl carbonate. The methanol concentration in the column top component $B_T$ was 91.43% by weight. Moreover, the column bottom component $B_B$, which was continuously withdrawn from the bottom 2 of the continuous multi-stage distillation column B at 9.3 ton/hr, contained not less than 99.99% by weight of dimethyl carbonate (methanol content not more than 0.01% by weight).

This means that of the dimethyl carbonate fed into the continuous multi-stage distillation column B, approximately 87.7% was obtained as high-purity dimethyl carbonate. Note that the column top component $B_T$ was fed as is into the reactive distillation column A, and thus used as some of the starting material for producing the dimethyl carbonate and the diol.

Prolonged continuous operation was carried out under these conditions. After 500 hours, 2000 hours, and 3000 hours, the produced amounts of dimethyl carbonate per hour were 9.3 ton, 9.3 ton, and 9.3 ton, and hence operation was very stable. The purity of the dimethyl carbonate obtained through the separation/purification was 99.99% in each case, and the halogen content was outside the detection limit, i.e. not more than 1 ppb.

INDUSTRIAL APPLICABILITY

According to the present invention, it has been discovered that, from out of a dialkyl carbonate and a diol produced through a reactive distillation system from a cyclic carbonate and an aliphatic monohydric alcohol, a high-purity dialkyl carbonate of purity not less than 97%, preferably not less than 99%, more preferably not less than 99.9%, can be obtained on an industrial scale of not less than 2 ton/hr, preferably not less than 3 ton/hr, more preferably not less than 4 ton/hr, with a high yield stably for a prolonged period of time of not less than 1000 hours, preferably not less than 3000 hours, more preferably not less than 5000 hours.

We claim:

1. In an industrial process for separating out a dialkyl carbonate, comprising the steps of:
    continuously feeding starting materials into a continuous multi-stage distillation column A in which a homogeneous catalyst is present by taking a cyclic carbonate and an aliphatic monohydric alcohol as the starting materials;
    carrying out reactive distillation in said column A;
    continuously withdrawing a high boiling point reaction mixture $A_B$ containing a produced diol from a lower portion of said column A in a liquid form;
    continuously withdrawing a low boiling point reaction mixture $A_T$ containing a produced dialkyl carbonate and the aliphatic monohydric alcohol from an upper portion of said column A in a gaseous form;
    continuously feeding said low boiling point reaction mixture $A_T$ into a continuous multi-stage distillation column B; and carrying out separation by distillation into a column top component $B_T$ having the aliphatic monohydric alcohol as a main component thereof and a column bottom component $B_B$ having the dialkyl carbonate as a main component thereof, wherein the improvement which comprises:

said continuous multi-stage distillation column B comprises a distillation column comprising a stripping section having a length $L_1$ (cm), an inside diameter $D_1$ (cm) and an internal with a number of stages $n_1$ thereinside, and an enrichment section having a length $L_2$ (cm), an inside diameter $D_2$ (cm) and an internal with a number of stages $n_2$ thereinside, wherein $L_1$, $D_1$, $n_1$, $L_2$, $D_2$, and $n_2$ satisfy the following formulae (1) to (8);

$$500 \leq L_1 \leq 3000 \quad (1)$$

$$100 \leq D_1 \leq 1000 \quad (2)$$

$$2 \leq L_1/D_1 \leq 30 \quad (3)$$

$$10 \leq n_1 \leq 40 \quad (4)$$

$$700 \leq L_2 \leq 5000 \quad (5)$$

$$50 \leq D_2 \leq 800 \quad (6)$$

$$10 \leq L_2/D_2 \leq 50 \quad (7), \text{ and}$$

$$35 \leq n_2 \leq 100 \quad (8).$$

2. The process according to claim 1, wherein $L_1$, $D_1$, $L_1/D_1$, $n_1$, $L_2$, $D_2$, $L_2/D_2$, and $n_2$ for said continuous multi-stage distillation column B satisfy $800 \leq L_1 \leq 2500$, $120 \leq D_1 \leq 800$, $5 \leq L_1/D_1 \leq 20$, $13 \leq n_1 \leq 25$, $1500 \leq L_2 \leq 3500$, $70 \leq D_2 \leq 600$, $15 \leq L_2/D_2 \leq 30$, $40 \leq n_2 \leq 70$, $L_1 \leq L_2$, and $D_2 \leq D_1$.

3. The process according to claim 1, wherein the internal in each of the stripping section and the enrichment section of said continuous multi-stage distillation column B is a tray and/or a packing.

4. The process according to claim 3, wherein the internal in each of the stripping section and the enrichment section of said continuous multi-stage distillation column B is the tray.

5. The process according to claim 4, wherein said tray is a sieve tray.

6. The process according to claim 5, wherein said sieve tray has 150 to 1200 holes/m² in a sieve portion thereof, and a cross-sectional area per hole is in a range of from 0.5 to 5 cm².

7. The process according to claim 5, wherein said sieve tray has 200 to 1100 holes/m² in said sieve portion thereof, and the cross-sectional area per hole is in a range of from 0.7 to 4 cm².

8. The process according to claim 5, wherein said sieve tray has 250 to 1000 holes/m² in said sieve portion thereof, and the cross-sectional area per hole is in a range of from 0.9 to 3 cm².

9. The process according to claim 1, wherein said continuous multi-stage distillation column B has a column bottom temperature in a range of from 150 to 250° C.

10. The process according to claim 1, wherein said continuous multi-stage distillation column B has a reflux ratio in a range of from 0.5 to 5.

11. The process according to claim 1, wherein a concentration of the dialkyl carbonate in said column bottom component $B_B$ is not less than 97% by weight based on 100% by weight of said column bottom component.

12. The process according to claim 1, wherein a concentration of the dialkyl carbonate in said column bottom component $B_B$ is not less than 99% by weight based on 100% by weight of said column bottom component.

13. The process according to claim 1, wherein a concentration of the dialkyl carbonate in said column bottom component $B_B$ is not less than 99.9% by weight based on 100% by weight of said column bottom component.

14. The process according to claim 1, wherein said column top component $B_T$ is recycled as a starting material for producing the dialkyl carbonate and the diol.

15. The process according to claim 1, wherein the cyclic carbonate comprises ethylene carbonate and/or propylene carbonate, the aliphatic monohydric alcohol comprises methanol and/or ethanol, and the dialkyl carbonate to be separated out comprises dimethyl carbonate and/or diethyl carbonate.

16. A dialkyl carbonate separated out by the process according to claim 1, which comprises a halogen content of not more than 0.1 ppm.

17. A dialkyl carbonate separated out by the process according to claim 1, which comprises a halogen content of not more than 1 ppb.

18. The dialkyl carbonate according to claim 16, which comprises an aliphatic monohydric alcohol content of not more than 0.1% by weight.

* * * * *